United States Patent [19]

Widmer

[11] Patent Number: Plant 7,381

[45] Date of Patent: Nov. 20, 1990

[54] CHRYSANTHEMUM PLANT NAMED SNOWSOTA

[75] Inventor: Richard E. Widmer, St. Paul, Minn.

[73] Assignee: Regents of the University of Minnesota, Minneapolis, Minn.

[21] Appl. No.: 274,404

[22] Filed: Nov. 21, 1988

[51] Int. Cl.[5] ..... A01H 5/00

[52] U.S. Cl. ..... Plt./77

[58] Field of Search ..... Plt. 77

*Primary Examiner*—Robert E. Bagwill

*Attorney, Agent, or Firm*—Merchant, Gould, Smith, Edell, Welter & Schmidt

[57] ABSTRACT

A new variety of *Dendranthema grandiflora* (*Chrysanthemum morifolium* Ramat.) for the outdoor garden and for spring flowering greenhouse pot plant culture, characterized by long-lasting blooms which are also early opening, 3.5 cm in diameter, full pompon, white with light yellow center, and resistant to pinking at lower temperatures, on plants of an informally mounded plant habit with small to medium sized leaves on stiff stems.

2 Drawing Sheets

BACKGROUND INFORMATION

This new cultivar of Chrysanthemum plant originated as seedling number 82-135-88 resulting from a cross of Spartan and Chiquita's Rival (unpatented cultivars) made in 1981 at St. Paul, Minn. during the course of breeding efforts in an on-going Chrysanthemum project under direction of the inventor, a professor at the University of Minnesota, Department of Horticultural Science and Landscape Architecture.

Minnesota Selection (NM Sel.) 82-135-88 was discovered and selected as one flowering plant within the progeny of the stated cross in the fall of 1982, in the St. Paul Campus field test plots at the University of Minnesota. The early opening of the 3.5 cm, white pompon flowers with light yellow centers, with the entire flower fading to a snow-white color and resistance to pinking at low temperatures, caused me to select this seedling for propagation and testing. The first act of asexual reproduction of MN Sel. 82-135-88 was accomplished when vegetative cuttings were taken in March–April 1983, in a controlled environment in St. Paul, Minn. Cuttings were from the initial selection plant that had been dug from the field in late October, 1982. Plants so reproduced continued to have the same favorable characteristics with clean, medium green foliage on stiff stems and white flowers with light yellow centers fading to a clear snow white color.

Plants of this Chrysanthemum were field tested at seven locations in Minnesota in 1985, 1986 and 1987, including the Minnesota Landscape Arboretum and the Crookston, Grand Rapids, Lamberton, Morris, Rosemount and Waseca Agricultural Experiment Stations. In addition, this cultivar was trialed in 1985, 1986 and 1987 as a greenhouse grown spring flowering plant in 3-inch pots. Rooted cuttings were potted March 15 of each year, pinched (stem tip removal) one week later and successfully forced into bloom in both natural (long day) and short day (0800–1600 hours) photoperiods. Flowering of this selection in the St. Paul Campus field test plots of the University of Minnesota usually begins in the last week of August and a week before the cultivar Baby Tears.

DESCRIPTION OF THE DRAWINGS

This new Chrysanthemum is illustrated by the accompanying photographs.

DESCRIPTION OF THE NEW PLANT

Figure 1:
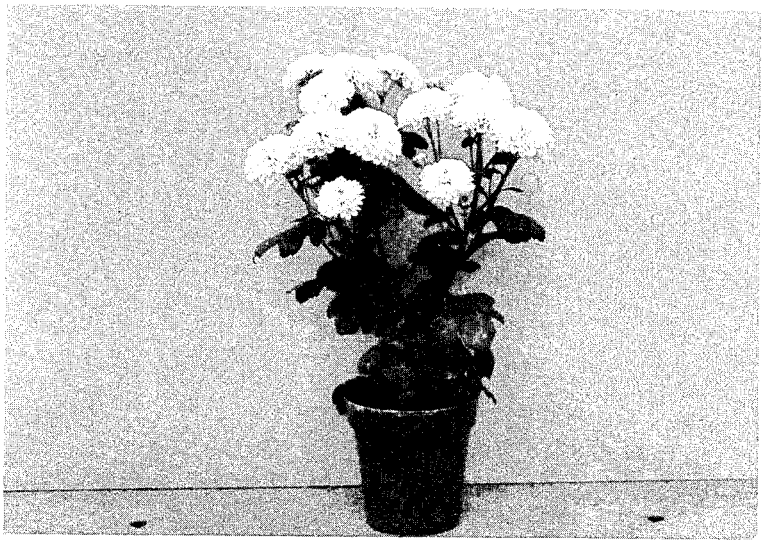
FIG. 1 is a black and white photo showing a greenhouse grown flowering plant in a 7.5 cm pot, photographed in May of 1988.
Figure 2:
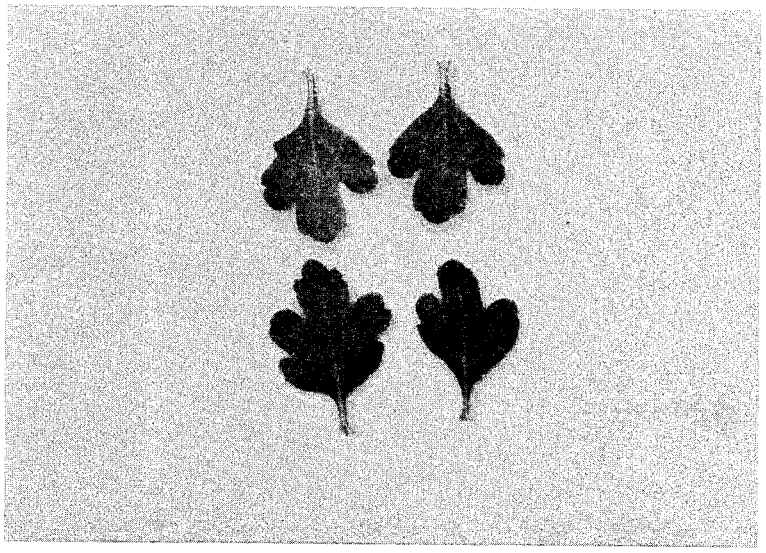
FIG. 2 is a black and white photo showing the under and upper surfaces of leaves from flowering plants of this cultivar.
Figure 3:
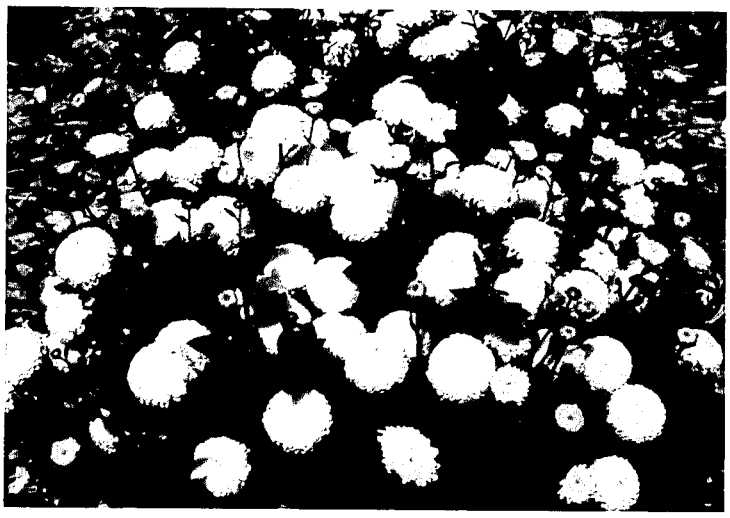
FIG. 3 is a color photograph of field grown plants in bloom in September, 1988, taken at the trial plots on the St. Paul Campus, University of Minnesota.

The following is a description of the new Chrysanthemum cultivar with color designations according to the R.H.S. Colour Chart published by The Royal Horticultural Society, London, England (copyright 1938). The observations were made of plants reproduced and grown at the trial plots on the St. Paul Campus, University of Minnesota, St. Paul, Minn.

THE PLANT

Origin: Seedling.

Parentage:

*Seed parent.*—Spartan (unpatented).

*Pollen parent.*—Chiquita's Rival (unpatented). Cultivar identified as MN Sel 82-135-88.

Classification:

*Botanic.*—*Dendranthema grandiflora* (*Chrysanthemum morifolium* Ramat.).

*Commercial.*—Greenhouse pot plant and outdoor garden plant.

Form: Perennial herbaceous bush.

Height:

*As a pot plant.*—10–19 cm above pot rim.

*As an outdoor garden plant.*—30 to 40 cm.

Growth: Terminal, spreading to form an informal mound, stiff stems.

Foliage: 7 to 8 leaves per 10 cm of stem.

*Leave size.*—About 5 cm across and 7.5 cm long.

*Shape.*—Ovate, lobed, generally incised.

*Color.*—Upper side-Spinach Green 960. Lower side-Spinach Green 960/2. Surface Texture: Puberulent. Venation: Pinnately veined. Petioles: About 2.2 cm in length.

THE BUD

Form: Elliptical.

Size:

*Diameter.*—0.7 to 8.0 cm.

*Depth.*—0.5 cm.

Opening: The bud opens slowly.

Color:

*When phyllaries first divide.*—Spinach Green 960/2.

*When florets begin to unfurl.*—Spinach Green 960/3.

Phyllaries: The outside of the receptacle bears many phyllaries as involucral bracts.

*Form.*—Spear shaped and curling up on edges.

*Color.*—Spinach Green 960/2, inside and outside.

*Surface texture.*—Puberulent.

*Penduncle.*—Length: 11 cm. Surface texture: puberulent.

*Strength.*—Firm.

*Color.*—Spinach Green 920/3.

THE FLOWER

Blooming:

*Capability.*—This plant can be flowered the year round with photoperiod temperature control.

*Response.*—6 weeks.

*Natural flowering season.*—August 26 to October 12.

Blooms:

*Flower type.*—Pompon.

*Size.*—Diameter — 3.5 cm. Depth — 2 cm. Center — 0.5 cm open center at maturity.

*Shape.*—Hermispherical becoming deeper at maturity.

*Born.*—Singly, as head of many florets on a receptacle, in a relatively open spray formation.

Florets: Numerous in quantity.

*Form.*—Broad obtuse, slight fringing at tips.

*Texture.*—Firm.

*Appearance.*—Clean, no shine.

*Arrangement.*—Pompon.

*Discoloration.*—Very little change; yellow center changes to white; minimum pinking at low temperatures.

| Color: | May | Sept |
|---|---|---|
| Outer Florets: | | |
| Upper side | White | white (a clean snow-whitecolor) |
| Reverse | White | White |
| Inside Florets: | | |
| Upper side | Sulfur yellow ½ | Sulfur yellow ½ |
| Reverse | Sulfur yellow ½ | Sulfur yellow 1/1 |

General color tonality: Clean snow-white at a distance of 6 feet.

Effect of weather: Flower is not effected by hot or wet weather.

Persistence: Florets hang on and dry.

Fragrance: Typical Chrysanthemum.

Lasting quality: 3–4 weeks.

REPRODUCTIVE ORGANS

Stamens: 10 to 25 attached to the receptacle in the center of the head.

*Filaments.*—Length — 0.3 cm. Color-Light yellow.

*Pollen.*—Color-Lemon Yellow 4.

Pistils:

*Number.*—One to each disc and ray floret, 0.2 cm long.

*Styles.*—About 0.15 to 0.2 cm long.

*Stigmas.*—Color-Canary yellow 2/2.

Ovaries: Interior bicarpellate.

I claim:

1. A new and distinct *Dendranthema grandiflora* cultivar substantially as shown and described herein, and particularly characterized by early opening florets, which are 3.5 cm in diameter, full, white with yellow center florets fading to white, the florets also being resistant to low temperature "pinking" with good lasting quality developing into informal mounds with clean foliage on stiff stems.

* * * * *

UNITED STATES PATENT AND TRADEMARK OFFICE

CERTIFICATE OF CORRECTION

PATENT NO. : Plant 7,381

DATED : November 20, 1990

INVENTOR(S) : Widmer

It is certified that error appears in the above-identified patent and that said Letters Patent is hereby corrected as shown below:

col. 1, line 12, for "NM" read --MN--.

col. 3, line 23, for "920/3" read --960/3--.

Signed and Sealed this

Twenty-sixth Day of October, 1993

*Attest:*

Bruce Lehman

BRUCE LEHMAN

*Attesting Officer*

*Commissioner of Patents and Trademarks*